US00PP20431P3

(12) United States Plant Patent

Southwick et al.

(10) Patent No.: US PP20,431 P3

(45) Date of Patent: Oct. 20, 2009

(54) APRICOT TREE NAMED 'MC5'

(50) Latin Name: *Prunus armeniaca*
Varietal Denomination: MC5

(75) Inventors: Stephen M. Southwick, Lodi, CA (US); David Decalo, Boulder, CO (US)

(73) Assignee: SDR Fruit, LLC, Boulder, CO (US)

( * ) Notice: Subject to any disclaimer, the term of this patent is extended or adjusted under 35 U.S.C. 154(b) by 110 days.

(21) Appl. No.: 12/002,747

(22) Filed: Dec. 18, 2007

(65) Prior Publication Data

US 2009/0158478 P1 Jun. 18, 2009

(51) Int. Cl.
*A01H 5/00* (2006.01)

(52) U.S. Cl. ..... Plt./186

(58) Field of Classification Search ..... Plt./186
See application file for complete search history.

*Primary Examiner*—Susan B McCormick Ewoldt
(74) *Attorney, Agent, or Firm*—Wells St John PS

(57) ABSTRACT

A new and distinct variety of apricot tree denominated varietally as 'MC5' is described herein and which produces an attractively colored apricot fruit which is mature for harvesting and shipment approximately May 14–May 22 under the ecological conditions prevailing in the San Joaquin Valley of central California.

5 Drawing Sheets

Botanical classification: *Prunus armeniaca.*

BACKGROUND OF THE NEW VARIETY

The present invention relates to a new, novel and distinct variety of apricot tree *'Prunus Armeniaca* L' which has been denominated varietally as 'MC5' hereinafter.

ASEXUAL REPRODUCTION

The present variety of apricot tree resulted from an open pollination of an apricot cultivar named 'OrangeRed' (unpatented), and which occurred within the cultivated region of our orchard which is located near Bakersfield, Calif. This occurred during the 1993 growing season. Seed derived from this open pollinated seedling was collected and then later germinated and planted in our orchard which was located near Vena, Calif. which is located in the northern portion of the San Joaquin Valley of California. The seedlings resulting from the seed derived from the original open pollinated cultivar of the 'OrangeRed' apricot tree showed promising characteristics and was thereafter selected for vegetative propagation. The inventors studied the fruit produced by the 'MC5' apricot tree during the 1996–1997 growing seasons. To confirm the characteristics of the present new variety of apricot tree, bud wood was removed from the promising seedlings and was then budded into 'Lovell' peach rootstock (unpatented) in 1998. These first asexually reproduced trees were then planted in our orchard which is located near Bakersfield, Calif. in the southern most region of the San Joaquin Valley.

These asexually reproduced test trees have been continually observed by the inventors and the fruit produced from these first asexually reproduced trees have been inspected and have been determined to be true to the original fruit produced by the parent tree, noted above. As a general matter, the trees of the new variety display vigorous growth, and further show no propensity for debilitating virus infections which are common in apricot varieties that are currently commercially grown.

In comparison to the 'OrangeRed' variety of apricot tree (unpatented) from which this new variety was derived as an opened pollinated seedling thereof, the present variety of apricot tree produces fruit which are larger in size, and firmer than the fruit produced from the 'OrangeRed' cultivar growing under the same environmental conditions as experienced in the Bakersfield, Calif. region of the San Joaquin Valley. Further, the new variety produces more consistent numbers of fruit when compared to other varieties of apricot trees growing in low chill growing areas such as the region surrounding Bakersfield, Calif.

SUMMARY OF THE NEW VARIETY

'MC5' is a new distinct variety of apricot tree which was derived from seed resulting from an open pollination of the 'OrangeRed' apricot tree (unpatented). The variety 'MC5' is noteworthy for producing fruit exhibiting a blush which covers about 40%–50% of the surface of the fruit. Still further, the fruit produced by the present variety is larger in size, and quite firm relative to the fruit produced by the 'OrangeRed' cultivar. In comparison to other known apricot varieties, 'MC5' is considered very productive, and ripens quite early in the season relative to other common apricot varieties. The present variety produces fruit which are available for harvesting and shipment at least 3 days earlier then the 'CastleBright' apricot tree (unpatented) which matures in approximately the same season. Still further, the present variety resists cracking occasioned by exposure to rain. In addition, the new variety 'MC5' is more colorful and flavorful than the fruit produced by the 'EarlyCot' apricot tree, U.S. Pat. No. 7,198; or the 'CastleBright' apricot tree (unpatented), both of which overlap with the ripening period of the present variety 'MC5'. As a general matter, the fruit produced by the 'MC5' apricot tree is good tasting, has a glabrous skin, is considered medium-large to large for the species, has a firm flesh and a round, clean suture line. The variety is productive, and its growth pattern is vigorous thereby requiring fruit thinning in some seasons. Additionally, the new variety has low chilling requirements, and appears to grow quite well in hot and arid environments such as the Bakersfield, Calif. area. This makes the present variety one of the earliest ripening, and most highly colored apricots that is currently commercially available.

BRIEF DESCRIPTION OF THE DRAWINGS

The accompanying drawings which are provided are a color photographs of the new variety of apricot tree and the fruit produced thereby.

DETAILED DESCRIPTION

Figure 1:
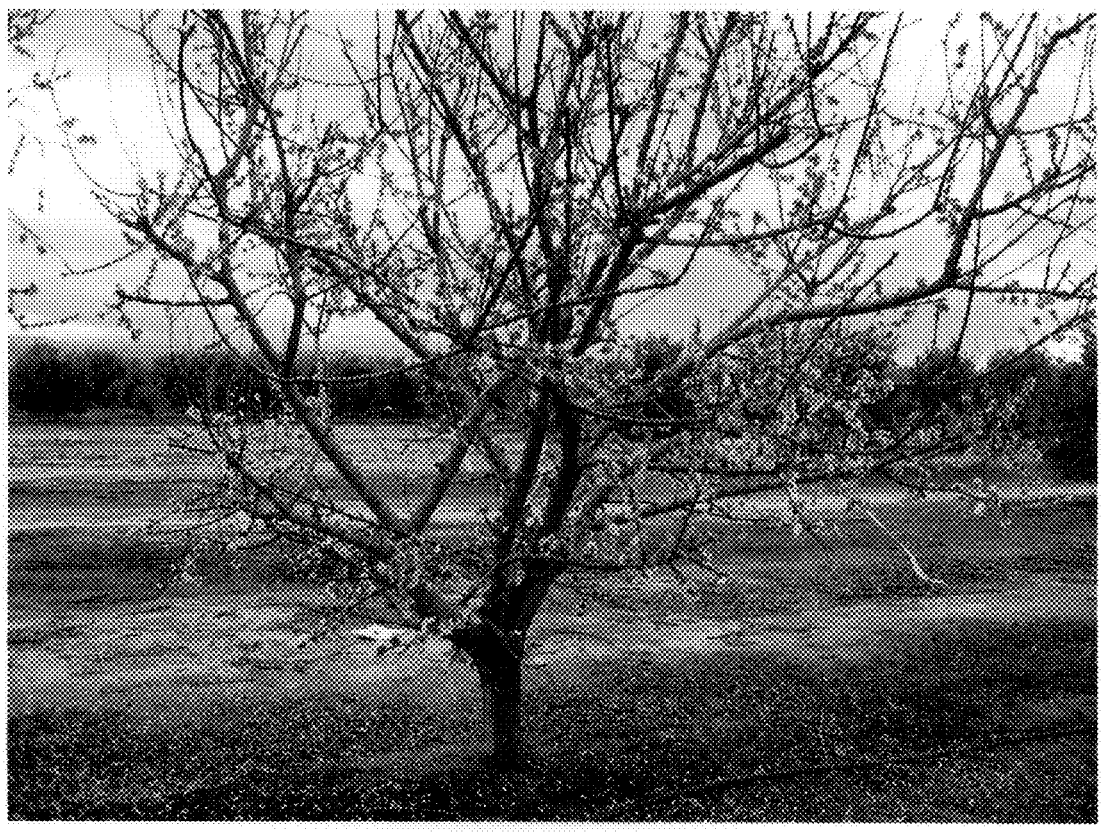
FIG. 1 shows the growth characteristics of a nine year old, second generation tree of the new variety 'MC5' which is growing on 'Lovell' rootstock (unpatented) and which displays its growth characteristics several days before full bloom as growing near Bakersfield, Calif.
Figure 2:
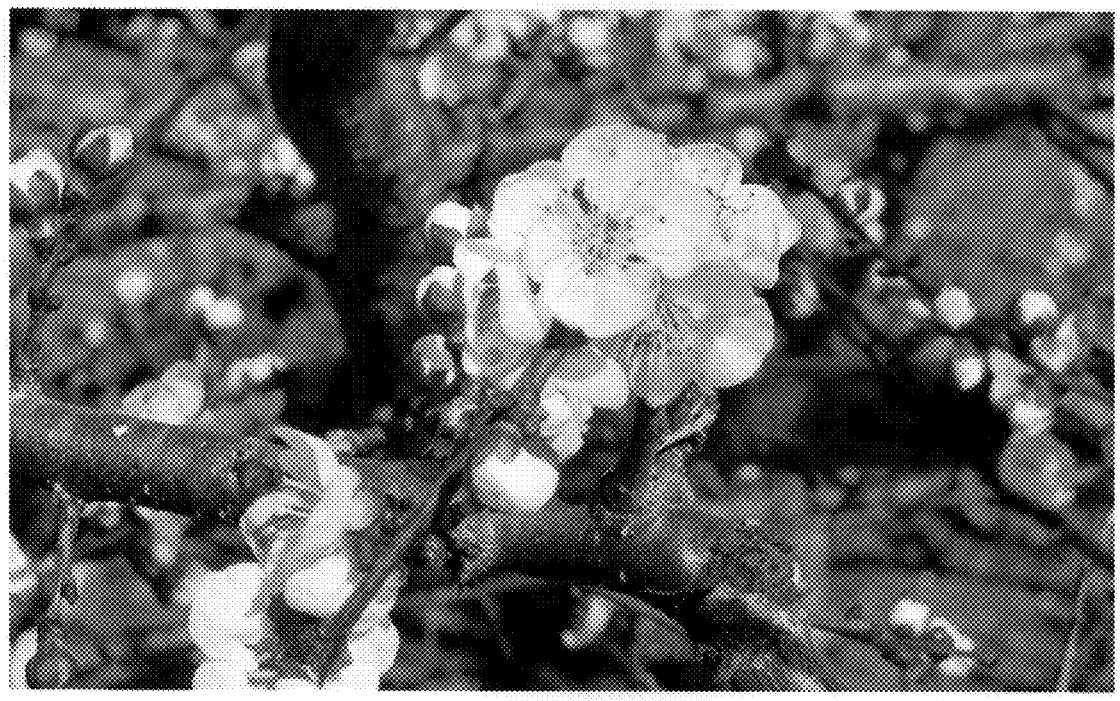
FIG. 2 shows a flower development stage of the new variety of apricot tree growing on current season wood.
Figure 3:
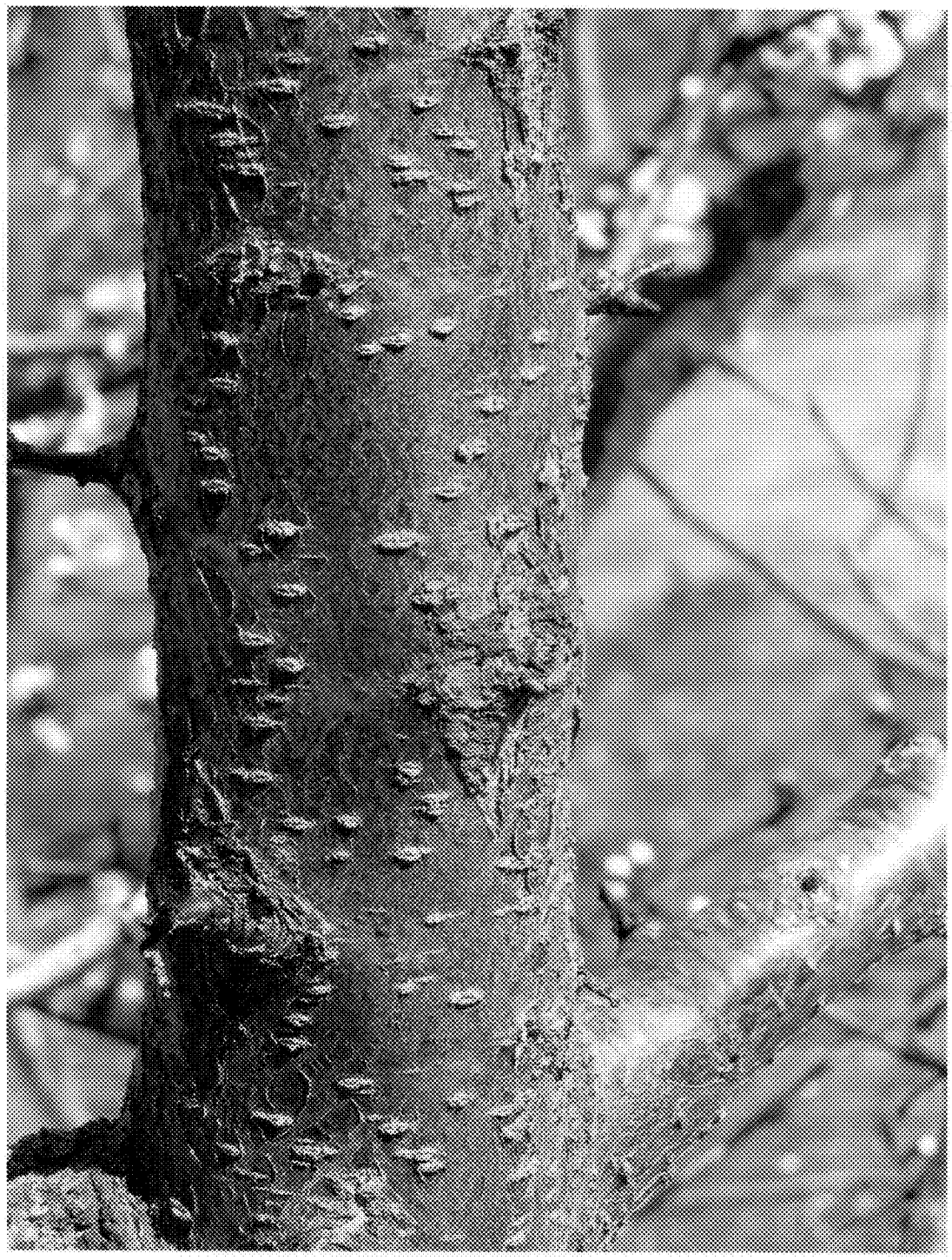
FIG. 3 shows the bark and lenticel characteristics of a nine year old, second generation tree which is located near Bakersfield, Calif.
Figure 4:
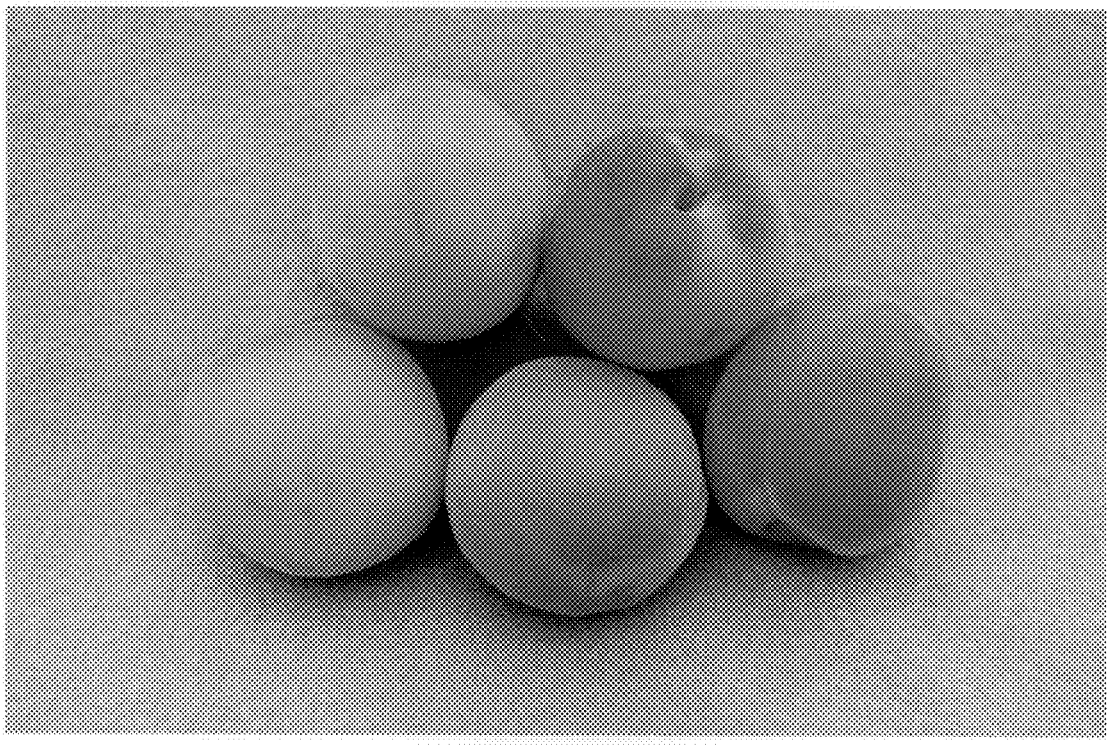
FIG. 4 shows several fruit of the new variety of apricot tree sufficiently matured for shipment.
Figure 5:
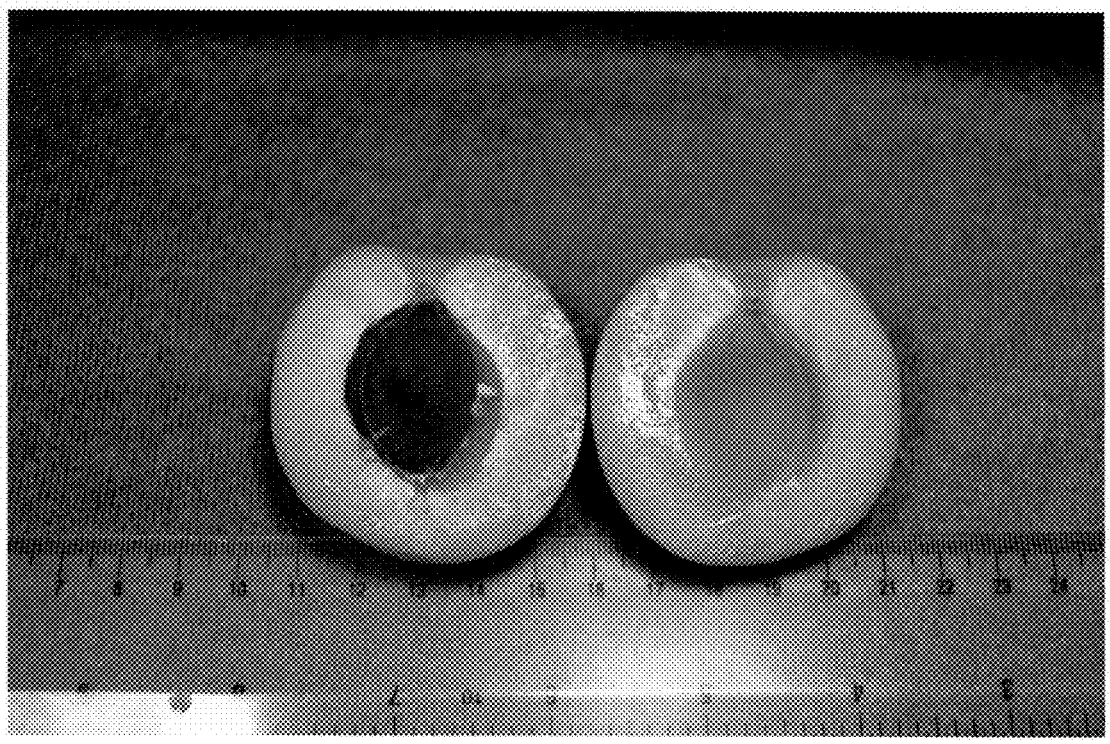
FIG. 5 shows the flesh and stone characteristics of several fruit of the new variety of apricot tree.

Referring more specifically to the pomological details of this new and distinct variety of apricot trees, the following has been observed on nine year old trees now growing under the ecological conditions prevailing at the orchards of the inventors which is located near Bakersfield, Calif. All major color code designations are by reference to The R.H.S. Colour Chart ($4^{th}$ Edition) provided by The Royal Horticultural Society of Great Britain. Common color names are also employed occasionally.

NOT A COMMERCIAL WARRANTY

The following detailed description has been prepared to solely comply with the provisions of 35 USC §112, and does not constitute a commercial warranty, (either expressed or implied), that the present variety will in the future display all the botanical, pomological or other characteristics as set forth, hereinafter. Therefore, this disclosure may not be relied upon to support any future legal claims including, but not limited to breach of warranty of merchantability, or fitness for any particular person which is directed, in whole or in part, to the present variety.

Tree:

*Size.*—Considered moderately high for the species and having an average height of about 5.5 meters, and an average circumference or crown spread of about 4.0 meters under the conditions prevailing at the orchards of the inventors which is located near Bakersfield, Calif. These measurements were secured from a tree which is 9 years old.

*Vigor.*—Generally considered vigorous with an annual growth habit of approximately 1 to 2 meters.

*Growth habit.*—Form — Considered upright and spreading. The present variety is pruned to a vase formed shape.

*Productivity.*—Generally — Considered productive for the variety.

*Pollination.*—Generally — The variety is not self-fruitful and therefore requires cross-pollination in order to produce fruit.

*Canopy density.*—Considered dense. The present variety's growth habit is such that pruning is needed to keep the variety in an open vase formed shape.

*Hardiness.*—Considered hardy under the typical growing conditions experienced in the Bakersfield, Calif. region.

*Chilling requirement.*—The present variety requires about 550–600 hours of chilling at a temperature below 7.2 degrees C. in order to set fruit. In comparison, the apricot variety 'OrangeRed' (unpatented) has a chilling requirement of about 1000 hours at the same temperature.

Trunk:

*Diameter.*—When measured at a distance of about 30 cm above the soil line, the diameter is about 35 cm.

*Bark texture.*—Considered rough for the species.

*Bark color.*—As a general matter, the surface ridge areas have a grey-purple color (Group N187B). Further, the valleys of the bark exhibit a grey-orange color (Group 164B).

*Scaffold branches.*—Generally — When measured at a distance of about 90 cm above the soil line, the scaffold branches have a bark texture that is considered smooth. However, with advancing senescence, the outer layers of the bark begin to peel back in small concentric patches.

*Scaffold branch color.*—Grey-purple (Group N187B).

*Lenticels.*—Generally — Present and having a rough texture. The lenticels of the present variety extend about 1–1.5 mm above the surface of the bark.

*Lenticels.*—Numbers — Generally 1–2 lenticels are found per square cm of bark surface.

*Lenticels size.*—Generally — About 2–3 mm in width, and about 3–5 mm in length.

*Lenticels.*—Color — Grey-white (Group 156D).

Branches:

*Length.*—The length of the flowering branches varies from about 5–35 cm. depending upon the environmental conditions existing during the growing season.

*Diameter.*—Approximately 0.55 cm when measured at the midpoint of the branch.

*Bark texture.*—Glabrous.

*Lenticels.*—Generally speaking, lenticels are present. These lenticels are considered few to moderate in number. The lenticels range in count from about 15 to about 25 per linear cm of branch length as measured at approximately the midpoint of the branch.

*Lenticel color.*—White (Group N155D).

*Internode length.*—About 1.54 cm to about 2.72 cm.

Leaves:

*Leaf buds.*—Shape — Considered ovoid.

*Leaf buds.*—Size — About 2.9 mm wide, and about 3.2 mm long.

*Leaf buds.*—Color — Grey-purple (N186C).

*Leaf form.*—Flat and broadly oval. The leaves are more serrulate then serrate.

*Leaf tip.*—Shape — Mucronate.

*Leaf base.*—Shape — Rounded.

*Leaf size.*—The average length of the leaf is about 98.7 mm. The average width is about 84 mm.

*Leaf thickness.*—Considered average for the species.

*Leaf color.*—Upper surface — Yellow-green (Group 147A).

*Leaf color.*—Lower surface — Yellow-green (Group 148B).

*Petiole.*—Size — The average length of the petiole is about 40.7 mm.
*Petiole.*—Diameter — About 1.56 mm.
*Petiole.*—Color — Yellow-green (Group 146D).
*Leaf glands.*—Generally — 0 to about 2 leaf glands may be found per petiole.
*Leaf glands.*—Shape — Globose and having a size of about 0.2 mm in width and about 1.5 mm in length.
*Leaf glands.*—Location — On the dorsal surface of the blade and some 5 mm to about 15 mm from the base.
*Leaf glands.*—Position — Where more than one leaf gland is present, both alternate and opposite leaf gland forms were observed.
*Leaf glands.*—Color — Black (Group 202A).
*Leaf stipules.*—Absent from the present variety.
*Leaf venation.*—Considered pinnately net veined.

Flower:

*Leaf buds.*—Generally — Leaf buds appear on one year old, and older wood. Typically two flower buds appear per node.
*Flower buds.*—Shape — Ovoid.
*Flower buds.*—Size — About 2.9 mm wide and about 4.7 mm long.
*Flower buds.*—Color — Grey-purple (Group N186C).
*Flower buds.*—2 Year Old Wood or Older — Typically appear more oval than ovoid.
*Flower buds.*—2 Year Old Wood Size — About 2.8 mm wide and about 3.0 mm long.
*Blooming time.*—First bloom was noted on Feb. 20, 2007. Further, full bloom was observed on Mar. 1, 2007 under the ecological conditions prevailing near Bakersfield, Calif.
*Floral fragrance.*—Generally — Aroma is mild and typical for apricot trees.
*Flower.*—Size — About 2.75 cm at full expansion.
*Peduncle.*—Length — About 0.2 mm to about 1.0 mm.
*Peduncle.*—Diameter — About 1.8 mm.
*Peduncle.*—Color — Green (Group 139D).
*Thalamus.*—Length — About 4.5 mm to about 6 mm.
*Thalamus.*—Diameter — About 4.7 mm.
*Thalamus.*—Color — Yellow-green (Group 150C). This color fades to a reddish-purple (Group 60A) at the region near the sepal attachment.
*Petals.*—Numbers — 5.
*Petals.*—Arrangement — Overlapping.
*Petals.*—Shape — Elliptical.
*Petals.*—Length — About 11.6 mm to about 13.7 mm.
*Petals.*—Width — About 14.6 mm to about 16.6 mm.
*Petals.*—Apex shape — Round.
*Petals.*—Base shape — Round, but narrows at the attachment point.
*Petals.*—Surface texture — Smooth.
*Petals.*—Marginal Form — Considered smooth.
*Petals.*—Color — White. This color is not distinctive of the present variety.
*Sepals.*—Numbers — 5.
*Sepals.*—Shape — Oval and having a cuspidate apex. The outer margins also cup inwardly.
*Sepals.*—Length — About 6 mm to about 8.9 mm.
*Sepals.*—Width — About 4.4 mm to 5.4 mm.
*Sepals.*—Surface texture — Glabrous.
*Sepals.*—Color — Red-purple (Group 60B).
*Stamens.*—Numbers — Variable from 30 to 36.
*Stamens.*—Length — About 8 mm.
*Filament length.*—About 6.5 mm.
*Average anther length.*—About 1.75 mm.
*Filament color.*—White (Group 155C).
*Anther color.*—Yellow (Group 12C).
*Pollen color.*—At full commercial maturity — Yellow (Group 12C).
*Pistil.*—Numbers — 1.
*Pistil.*—Average Length — 15.9 mm.
*Ovary.*—Diameter — About 2.6 mm.
*Ovary color.*—Green-yellow (Group 1D).
*Ovary pubescence.*—Present.
*Stigma.*—Length — About 11.9 mm.
*Stigma.*—Color — Green-yellow (Group 1A).

Fruit:

*Maturity when described.*—Firm, ripe condition (shipping ripe).
*Date of first picking.*—May 14, 2007.
*Date of last picking.*—May 22, 2007. The date and duration of the harvest varies slightly with the prevailing climatic conditions. The present variety was harvested under the conditions then prevailing at the orchard of the inventors which is located near Bakersfield, Calif. in the San Joaquin Valley of California. The present variety is harvested some 2–3 days earlier than the apricot variety 'OrangeRed' (unpatented) at the same geographic location.
*Fruit size.*—Generally — Considered large for the species.
*Fruit length.*—About 55.1 mm.
*Fruit diameter.*—When measured in the suture plane, it is about 53.6 mm. When measured perpendicular to the suture plane, it is about 48.2 mm.
*Fruit weight.*—Generally — About 75.6 grams. This is greater than the fruit weight produced by the 'OrangeRed' variety which have an average weight of about 55 grams.
*Fruit shape.*—Generally — Considered round to slightly round and oblong.
*Stem cavity.*—Size — About 13.4 mm. wide and about 9.2 mm deep.
*Stem cavity.*—Surface Texture — No tearing was observed.
*Stem retention.*—Generally — Approximately 25% of the stem is retained.
*Suture.*—Generally — Considered distinct, and ranging from about 1 mm to about 1.7 mm in depth.
*Fruit skin.*—Surface texture — Glabrous.
*Fruit skin.*—Thickness — Considered thin and tender for the species. The fruit skin is considered melting.
*Fruit skin.*—Pubescence — Present, but considered very fine.
*Fruit skin.*—Background color — Orange (Group 26A). Exposed fruit have an additional blush color that develops over 35% to 45% of the fruit skin surface. The blush color is red (Group N34A). In comparison, the fruit produced by the 'OrangeRed' variety of apricot tree has a blush that covers only about 30% of the fruit surface.
*Tendency to crack.*—Not observed.
*Flesh color.*—Orange (Group 26A).
*Sugar content.*—On average the fruit of the present variety produces a brix of about 13.4 degrees. In comparison, the 'OrangeRed' variety produces fruit having a brix of about 11.6 degrees.
*Flesh aroma.*—Average and typical of apricots.
*Flesh flavor.*—Considered mild, sweet and sub-acidic.

*Flesh texture.*—Considered firm and moderately crisp.

*Flesh fibers.*—Present and moderate in number. The flesh fibers are short and indistinct.

*Eating quality.*—Generally considered excellent.

Stone:

*Attachment.*—Generally — Considered freestone.

*Stone size.*—Length — About 30.7 mm.

*Stone size.*—Diameter — When measured in line with the suture plane, about 21.4 mm. When measured perpendicular to the suture plane, it is about 12.1 mm.

*Stone.*—Color — When fully dry, the stone has a grey-orange color (Group 164B).

*Stone cavity.*—Length — About 33 mm.

*Stone cavity.*—Width — About 25.1 mm.

*Stone.*—Form — Considered generally more oblong than oval. The stone has substantially equal sides when measured on the opposite sides of the suture line.

*Stone base.*—Shape — Considered more conic than round.

*Stone apex.*—Generally considered round and sometimes exhibiting slight beaking.

*Stone ridges.*—Generally — 3 ridges are present and are quite distinct. As a general matter, the outside ridges are less sharp and distinct then the center ridge.

*Stone ridges.*—Dimensions — The distance between the outside ridges at their widest point averages about 6.6 mm.

*Stone surface.*—Generally — Considered textured.

*Tendency to split.*—Not observed.

*Resistance to insects and diseases.*—No particular susceptibilities were noted. The present variety has not been tested to expose or detect any susceptibilities or resistances of any known plant and/or fruit diseases.

Although the new variety of apricot tree possesses the described characteristics when grown under the ecological conditions prevailing near Bakersfield, Calif. in the San Joaquin Valley of California, it should be understood that variations of the usual magnitude and characteristics incident to changes in growing conditions, fertilization, pruning, pest control and horticultural management are to be expected.

Having thus described and illustrated our new variety of apricot tree, what we claim is new, and desire to secure by Plant Letters Patent is:

1. A new and distinct variety of apricot tree substantially as illustrated and described and which is characterized principally as to novelty by producing an attractively colored apricot which is mature for harvesting and shipment approximately May 14–May 22 under the ecological conditions prevailing near Bakersfield, Calif.

* * * * *